United States Patent
Baker

(10) Patent No.: US 9,055,998 B2
(45) Date of Patent: *Jun. 16, 2015

(54) BARIATRIC DEVICE AND METHOD FOR RECIPIENT WITH ALTERED ANATOMY

(75) Inventor: Randal S. Baker, Ada, MI (US)

(73) Assignee: BFKW, LLC, Grand Rapids, MI (US)

( * ) Notice: Subject to any disclaimer, the term of this patent is extended or adjusted under 35 U.S.C. 154(b) by 395 days.

This patent is subject to a terminal disclaimer.

(21) Appl. No.: 13/556,502

(22) Filed: Jul. 24, 2012

(65) Prior Publication Data

US 2012/0289991 A1 Nov. 15, 2012

Related U.S. Application Data

(63) Continuation-in-part of application No. PCT/US2011/023306, filed on Feb. 1, 2011, and a continuation-in-part of application No. 13/331,425, filed on Dec. 20, 2011, now Pat. No. 8,672,831, which (Continued)

(51) Int. Cl.
*A61F 2/04* (2013.01)
*A61F 5/00* (2006.01)

(52) U.S. Cl.
CPC .............. *A61F 2/04* (2013.01); *A61F 2002/045* (2013.01); *A61F 5/0069* (2013.01); *A61F 5/0013* (2013.01); *A61F 5/0076* (2013.01); *A61F 2002/044* (2013.01)

(58) Field of Classification Search
CPC ....... A61F 2/04; A61F 5/0076; A61F 5/0013; A61F 2002/045; A61F 5/0069
USPC .......... 128/898; 623/1.1, 11.11, 23.64, 23.65; 600/97, 37; 606/213–219, 139, 192, 606/191; 604/104–109, 99.01, 500, 909
See application file for complete search history.

(56) References Cited

U.S. PATENT DOCUMENTS

| 4,403,604 A | 9/1983 | Wilkinson et al. |
| 4,607,618 A | 8/1986 | Angelchik |

(Continued)

FOREIGN PATENT DOCUMENTS

| RU | 2045233 C1 | 10/1995 |
| RU | 94026119 A1 | 8/1996 |

(Continued)

OTHER PUBLICATIONS

International Preliminary Report on Patentability from corresponding Patent Cooperation Treaty Patent Application No. PCT/US2011/023306 mailed Aug. 16, 2012.

(Continued)

*Primary Examiner* — Manuel Mendez
(74) *Attorney, Agent, or Firm* — Gardner, Linn, Burkhart & Flory, LLP

(57) ABSTRACT

A bariatric device and method of causing at least partial satiety in a recipient that either has or is presently undergoing a procedure that alters the anatomy of the recipient includes deploying a bariatric device to the recipient having an altered anatomy. The bariatric device includes a cardiac member having a cardiac surface that is configured to generally conform to the shape and size of a portion of the cardiac region of the stomach of the recipient. The cardiac member stimulates receptors with the cardiac surface in order to influence a neurohormonal mechanism in the recipient sufficient to cause at least partial satiety by augmenting fullness caused by food and simulating fullness in the absence of food.

22 Claims, 9 Drawing Sheets

Related U.S. Application Data is a continuation of application No. 12/915,952, filed on Oct. 29, 2010, now Pat. No. 8,100,931, which is a continuation of application No. 11/463,192, filed on Aug. 8, 2006, now Pat. No. 7,846,174, which is a continuation-in-part of application No. PCT/US2005/036991, filed on Oct. 13, 2005.

(60) Provisional application No. 61/300,674, filed on Feb. 2, 2010, provisional application No. 61/301,373, filed on Feb. 4, 2010, provisional application No. 60/619,308, filed on Oct. 15, 2004, provisional application No. 60/632,147, filed on Dec. 1, 2004, provisional application No. 60/636,845, filed on Dec. 15, 2004, provisional application No. 60/711,310, filed on Aug. 25, 2005.

(56) References Cited

U.S. PATENT DOCUMENTS

| | | | |
|---|---|---|---|
| 5,234,454 A | 8/1993 | Bangs | |
| 5,306,300 A | 4/1994 | Berry | |
| 5,662,713 A * | 9/1997 | Andersen et al. | 128/898 |
| 5,820,584 A | 10/1998 | Crabb | |
| 6,146,416 A | 11/2000 | Andersen et al. | |
| 6,355,070 B1 | 3/2002 | Andersen et al. | |
| 6,432,040 B1 | 8/2002 | Meah | |
| 6,558,400 B2 | 5/2003 | Deem et al. | |
| 6,572,627 B2 | 6/2003 | Gabbay | |
| 6,656,194 B1 | 12/2003 | Gannoe et al. | |
| 6,675,809 B2 | 1/2004 | Stack et al. | |
| 6,740,121 B2 | 5/2004 | Geitz | |
| 6,746,460 B2 | 6/2004 | Gannoe et al. | |
| 6,755,869 B2 | 6/2004 | Geitz | |
| 6,773,440 B2 | 8/2004 | Gannoe et al. | |
| 6,802,868 B2 | 10/2004 | Silverman et al. | |
| 6,845,776 B2 | 1/2005 | Stack et al. | |
| 6,960,233 B1 | 11/2005 | Berg et al. | |
| 6,981,978 B2 | 1/2006 | Gannoe | |
| 6,994,095 B2 | 2/2006 | Burnett | |
| 6,994,715 B2 | 2/2006 | Gannoe et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,044,979 B2 | 5/2006 | Silverman et al. | |
| 7,066,945 B2 | 6/2006 | Hashiba et al. | |
| 7,083,629 B2 | 8/2006 | Weller et al. | |
| 7,087,088 B2 | 8/2006 | Berg et al. | |
| 7,097,650 B2 | 8/2006 | Weller et al. | |
| 7,097,665 B2 | 8/2006 | Stack et al. | |
| 7,146,984 B2 | 12/2006 | Stack et al. | |
| 7,152,607 B2 | 12/2006 | Stack et al. | |
| 7,220,284 B2 | 5/2007 | Kagan et al. | |
| 7,232,461 B2 | 6/2007 | Ramer | |
| 7,347,875 B2 | 3/2008 | Levine et al. | |
| 7,431,725 B2 | 10/2008 | Stack et al. | |
| 7,445,010 B2 | 11/2008 | Kugler et al. | |
| 7,682,330 B2 | 3/2010 | Meade et al. | |
| 7,708,752 B2 | 5/2010 | Durgin | |
| 7,771,382 B2 | 8/2010 | Levine et al. | |
| 7,815,589 B2 | 10/2010 | Meade et al. | |
| 7,815,591 B2 | 10/2010 | Levine et al. | |
| 7,846,174 B2 * | 12/2010 | Baker et al. | 606/191 |
| 7,976,488 B2 | 7/2011 | Levine et al. | |
| 7,981,163 B2 | 7/2011 | Meade et al. | |
| 8,029,455 B2 | 10/2011 | Stack et al. | |
| 8,043,355 B2 | 10/2011 | Shin et al. | |
| 8,100,931 B2 * | 1/2012 | Baker et al. | 606/191 |
| 8,137,301 B2 | 3/2012 | Levine et al. | |
| 8,162,871 B2 | 4/2012 | Levine et al. | |
| 8,282,598 B2 | 10/2012 | Belhe et al. | |
| 8,529,431 B2 | 9/2013 | Baker et al. | |
| 8,672,831 B2 * | 3/2014 | Baker et al. | 600/37 |
| 8,894,670 B2 | 11/2014 | Baker et al. | |
| 2002/0091395 A1 | 7/2002 | Gabbay | |
| 2003/0040804 A1* | 2/2003 | Stack et al. | 623/23.7 |
| 2003/0040808 A1 | 2/2003 | Stack et al. | |
| 2004/0117031 A1 | 6/2004 | Stack et al. | |
| 2004/0143342 A1 | 7/2004 | Stack et al. | |
| 2004/0148034 A1* | 7/2004 | Kagan et al. | 623/23.65 |
| 2004/0172141 A1 | 9/2004 | Stack et al. | |
| 2004/0220682 A1 | 11/2004 | Levine et al. | |
| 2005/0080395 A1 | 4/2005 | Levine et al. | |
| 2005/0096728 A1 | 5/2005 | Ramer | |
| 2005/0125020 A1 | 6/2005 | Meade et al. | |
| 2005/0197715 A1 | 9/2005 | Kugler et al. | |
| 2005/0228504 A1 | 10/2005 | Demarais | |
| 2005/0245788 A1 | 11/2005 | Gerber | |
| 2005/0245957 A1 | 11/2005 | Starkebaum et al. | |
| 2005/0247320 A1 | 11/2005 | Stack et al. | |
| 2005/0283235 A1 | 12/2005 | Kugler et al. | |
| 2006/0020277 A1 | 1/2006 | Gostout et al. | |
| 2006/0064120 A1 | 3/2006 | Levine et al. | |
| 2006/0074473 A1 | 4/2006 | Gertner | |
| 2006/0089571 A1 | 4/2006 | Gertner | |
| 2006/0142844 A1 | 6/2006 | Lowe et al. | |
| 2006/0155375 A1 | 7/2006 | Kagan et al. | |
| 2006/0161139 A1 | 7/2006 | Levine et al. | |
| 2006/0190019 A1 | 8/2006 | Gannoe et al. | |
| 2006/0265082 A1 | 11/2006 | Meade et al. | |
| 2007/0005147 A1 | 1/2007 | Levine et al. | |
| 2007/0010866 A1 | 1/2007 | Dann et al. | |
| 2007/0166396 A1 | 7/2007 | Badylak et al. | |
| 2007/0276432 A1 | 11/2007 | Stack et al. | |
| 2008/0015523 A1 | 1/2008 | Baker | |
| 2008/0065136 A1 | 3/2008 | Young | |
| 2008/0312678 A1 | 12/2008 | Pasricha | |
| 2009/0177215 A1 | 7/2009 | Stack et al. | |
| 2009/0240340 A1 | 9/2009 | Levine et al. | |
| 2009/0248171 A1 | 10/2009 | Levine et al. | |
| 2010/0030017 A1 | 2/2010 | Baker et al. | |
| 2010/0063518 A1 | 3/2010 | Baker et al. | |
| 2010/0114130 A1 | 5/2010 | Meade et al. | |
| 2010/0198237 A1 | 8/2010 | Baker et al. | |
| 2011/0009690 A1 | 1/2011 | Belhe et al. | |
| 2012/0089168 A1 | 4/2012 | Baker et al. | |
| 2013/0296913 A1 | 11/2013 | Foote et al. | |

FOREIGN PATENT DOCUMENTS

| | | |
|---|---|---|
| WO | 9412136 A1 | 6/1994 |
| WO | 2004064685 A1 | 8/2004 |
| WO | 2005037152 A1 | 4/2005 |
| WO | 2011116025 A1 | 9/2011 |

OTHER PUBLICATIONS

"Obesity: Super-Sized Medical Device Market", Start-Up, Mar. 2003, Technology Strategies (Long Article), pp. 1-10.

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, pp. 1-2 and p. 1 of 2 (2004).

Andrew F.R. Dixon, John B. Dixon, and Paul E. O'Brien, "Laparoscopic Adjustable Gastric Banding Induces Prolonged Satiety: A Randomized Blind Crossover Study", The Journal of Clinical Endocrinology & Metabolism, pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Information pertaining to inventorship of the various claims and lack of obligation to assign (Jan. 5, 2010).

International Search Report and Written Opinion of the International Searching Authority from corresponding Patent Cooperation Treaty (PCT) Application No. PCT/US05/36991, mailed Mar. 31, 2006.

(56) References Cited

OTHER PUBLICATIONS

Summary of Official Action dated Oct. 29, 2009, from the Israel Patent Office in a patent application corresponding to the present application.
Lowe, Andrew S., M.D. and Sheridan, Maria B., M.D., "Esophageal Stenting," annotated by Israel Patent Office (2004).
Abstract and claims of U.S. Patent 6,960,233 annotated by the Israel Patent Office (Nov. 1, 2005).
International Search Report and Written Opinion of the International Searching Authority from corresponding Patent Cooperation Treaty (PCT) Application No. PCT/US2011/023306, mailed Mar. 17, 2011.
Commonly assigned copending U.S. Appl. No. 14/118,731, filed Nov. 19, 2013.
Commonly assigned copending U.S. Appl. No. 14/518,414, filed Oct. 20, 2014, entitled Mucosal Capture Fixation of Medical Device.
Schembre, Drew, "Advances in Esophageal Stenting: the Evolution of Fully Covered Stents for Malignant and Benign Disease," Adv. Ther., Springer Healthcare, Apr. 1, 2010, pp. 1-13.
Commonly assigned copending U.S. Appl. No. 14/572,230, filed Dec. 16, 2014, entitled Endoscopic Fixation of a Medical Device Using Mucosal Capture.

* cited by examiner

BARIATRIC DEVICE AND METHOD FOR RECIPIENT WITH ALTERED ANATOMY

CROSS REFERENCE TO RELATED APPLICATIONS

This application is a continuation-in-part of International Patent Application No. PCT/US11/23306 filed on Feb. 1, 2011, which claims the benefit of U.S. provisional patent application Ser. No. 61/300,674 filed on Feb. 2, 2010, and claims the benefit of U.S. provisional patent application Ser. No. 61/301,373 filed on Feb. 4, 2010, and this application is a continuation-in-part of U.S. patent application Ser. No. 13/331,425 filed on Dec. 20, 2011, which is a continuation of U.S. patent application Ser. No. 12/915,952 filed on Oct. 29, 2010, now U.S. Pat. No. 8,100,931, which is a continuation of U.S. patent application Ser. No. 11/463,192 filed on Aug. 8, 2006, now U.S. Pat. No. 7,846,174, which is continuation-in-part of International Patent Application No. PCT/US05/36991 filed on Oct. 13, 2005, which claims the benefit of U.S. provisional patent application Ser. No. 60/619,308 filed on Oct. 15, 2004, and claims the benefit of U.S. provisional patent application Ser. No. 60/632,147 filed on Dec. 1, 2004, and claims the benefit of U.S. provisional patent application Ser. No. 60/636,845 filed on Dec. 15, 2004, and claims the benefit of U.S. provisional patent application Ser. No. 60/711,310 filed on Aug. 25, 2005, the disclosures of which are incorporated herein by reference in their entirety.

BACKGROUND OF THE INVENTION

The present invention is directed to a bariatric device and method of causing weight loss in a recipient.

Obesity is a large and increasing problem in the United States and worldwide. In round numbers, from the period encompassing the year 1990 to the period encompassing the year 2000, the prevalence of overweight people (BMI greater than 25) increased from 56 percent of United States adults to 65 percent and the prevalence of obese adults (BMI greater than 30) increased from 23 percent to 30 percent. Likewise, the prevalence of overweight children and adolescents (ages 6-19 years) increased from 11 percent in the period encompassing the year 1990 to 16 percent in the period encompassing the year 2000. The increasing prevalence of excess body mass among children and adolescents will make the problem even greater when they reach adulthood. The problem is not limited to the United States. Between 10 percent and 20 percent of European men are obese, and between 10 percent and 25 percent of European women are obese. Numerous medical conditions are made worse by obesity, including Type II diabetes, stroke, gallbladder disease, and various forms of cancer. Approximately 500,000 people in North America and Western Europe are estimated to die from obesity-related diseases every year and obesity is estimated to affect more than one billion adults worldwide. Therefore, there is a pressing and unmet need for a solution to the epidemic problem.

SUMMARY OF THE INVENTION

A bariatric device and method of causing at least partial satiety in a recipient that either has or is presently undergoing a procedure that alters the anatomy of the recipient, according to an aspect of the invention, includes deploying a bariatric device to the recipient having an altered anatomy. The bariatric device includes a cardiac member having a cardiac surface that is configured to generally conform to the shape and size of a portion of the cardiac region of the stomach of the recipient. The cardiac member stimulates receptors with the cardiac surface in order to influence a neurohormonal mechanism in the recipient sufficient to cause at least partial satiety by augmenting fullness caused by food and simulating fullness in the absence of food.

The device may be deployed to a recipient having undergone a bariatric procedure, such as (i) a gastric bypass procedure, (ii) a vertical banded gastroplasty, (iii) a sleeve gastrectomy, (iv) a duodenal switch, or (v) a laparoscopic gastric band, whether the procedure is performed laparoscopically, endoscopically, or the like.

The cardiac member may have a self-expanding surface. The self-expanding surface may be in the form of a scroll shaped to allow the self-expanding surface to be contracted in a roll, such as for deployment and unrolled to engage the walls of the stomach. The bariatric device may further include an esophageal member having an esophageal surface that is configured to generally conform to the shape and size of a portion of the esophagus and a connector connected with said esophageal member and said cardiac member.

The cardiac surface may be adjustable in order to adjust the amount of stimulus applied to the cardiac portion of the stomach. Adjustment may be made concurrently with deployment or subsequent to deployment. Adjustment may be performed endoscopically via a radio frequency link, or the like.

Anti-migration of the cardiac member may be provided. The anti-migration may include providing a surface having tissue adhesion and/or tissue ingrowth characteristics. The anti-migration may include sizing the cardiac member to be generally larger in shape than a stoma of the native stomach. The anti-migration may include mucosa capture. The anti-migration may include a projection from the cardiac member that is configured to extend to the esophagus or the intestine of the recipient to resist misorientation of the bariatric device.

The bariatric device and method may be applied to a recipient who had previously undergone bariatric surgery to produce the altered anatomy. Alternatively, the bariatric device and method may be applied concurrently with altering the anatomy of the recipient.

These and other objects, advantages and features of this invention will become apparent upon review of the following specification in conjunction with the drawings.

DESCRIPTION OF THE PREFERRED EMBODIMENT

Figure 1:
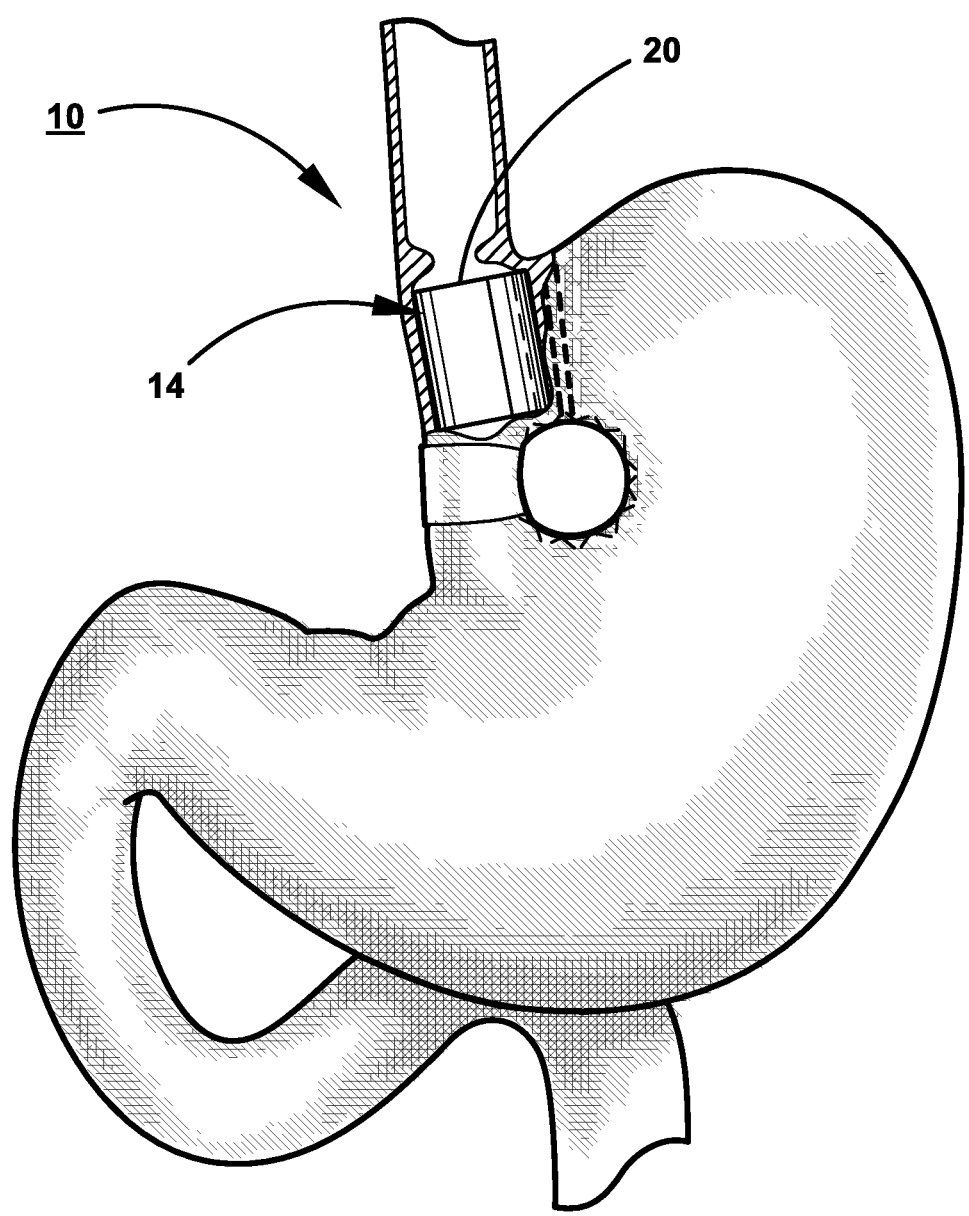
FIG. 1 is a perspective view illustrating deployment of a bariatric device in a recipient who underwent or is undergoing a vertical banded gastroplasty.

Referring now to the drawings and the illustrative embodiments depicted therein, a bariatric device of the various embodiments disclosed herein may be applied to a recipient that has an altered anatomy, such as from bariatric surgery. Such bariatric device stimulates receptors at least in the native stomach, or pouch, in order to influence a neurohormonal mechanism in the recipient sufficient to cause at least partial satiety by augmenting fullness caused by food and simulating fullness in the absence of food. Such bariatric device may be applied, for example, to a recipient who had previously undergone bariatric surgery, but is now experiencing difficulty with lack of satiety including weight gain. Alternatively, such bariatric device may be deployed to a recipient who is presently undergoing bariatric surgery to enhance the effect of the surgery and avoid lack of satiety in the future. The altered anatomy may be a result of procedures other than bariatric procedures, such as stomach surgery for cancer, or the like. Also, the altered anatomy may be performed using open surgery, laparoscopic surgery, or endoscopic surgery.

Bariatric device 10 has a cardiac member 14 that is configured to the functional portion of the stomach component of the altered anatomy to provide a tension, such as an outward pressure. Cardiac member 14 has a wall 20 configured to the size and shape of the cardiac region of a stomach that has undergone vertical banded gastroplasty (FIG. 1). The outer surface of wall 20 applies a strain to the cardiac region of the stomach to stimulate receptors to influence the neurohormonal feedback mechanism in a manner that causes at least partial satiety by augmenting fullness caused by food and simulating fullness in the absence of food as disclosed in commonly assigned U.S. Pat. No. 7,846,174, the disclosure of which is hereby incorporated herein reference. Cardiac member 14 may be partially or wholly the size of the functional portion of the stomach in the form of a pouch. If cardiac member 14 is larger than the stoma of the pouch, the cardiac member will avoid distal migration through the stoma.

Figure 2:
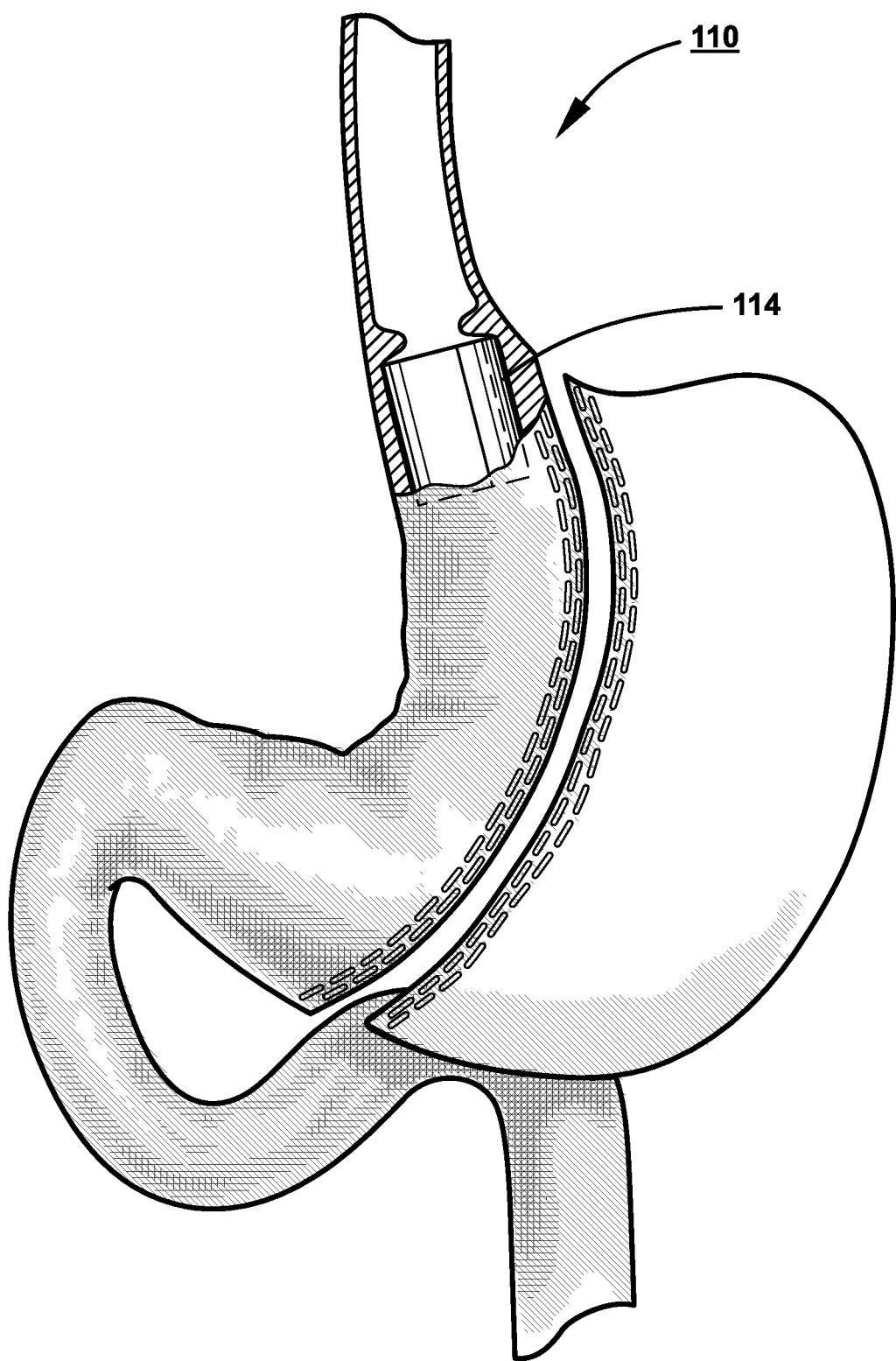
FIG. 2 is a perspective-view illustrating deployment of a bariatric device in a recipient who underwent or is undergoing a sleeve gastrectomy.
Figure 3:
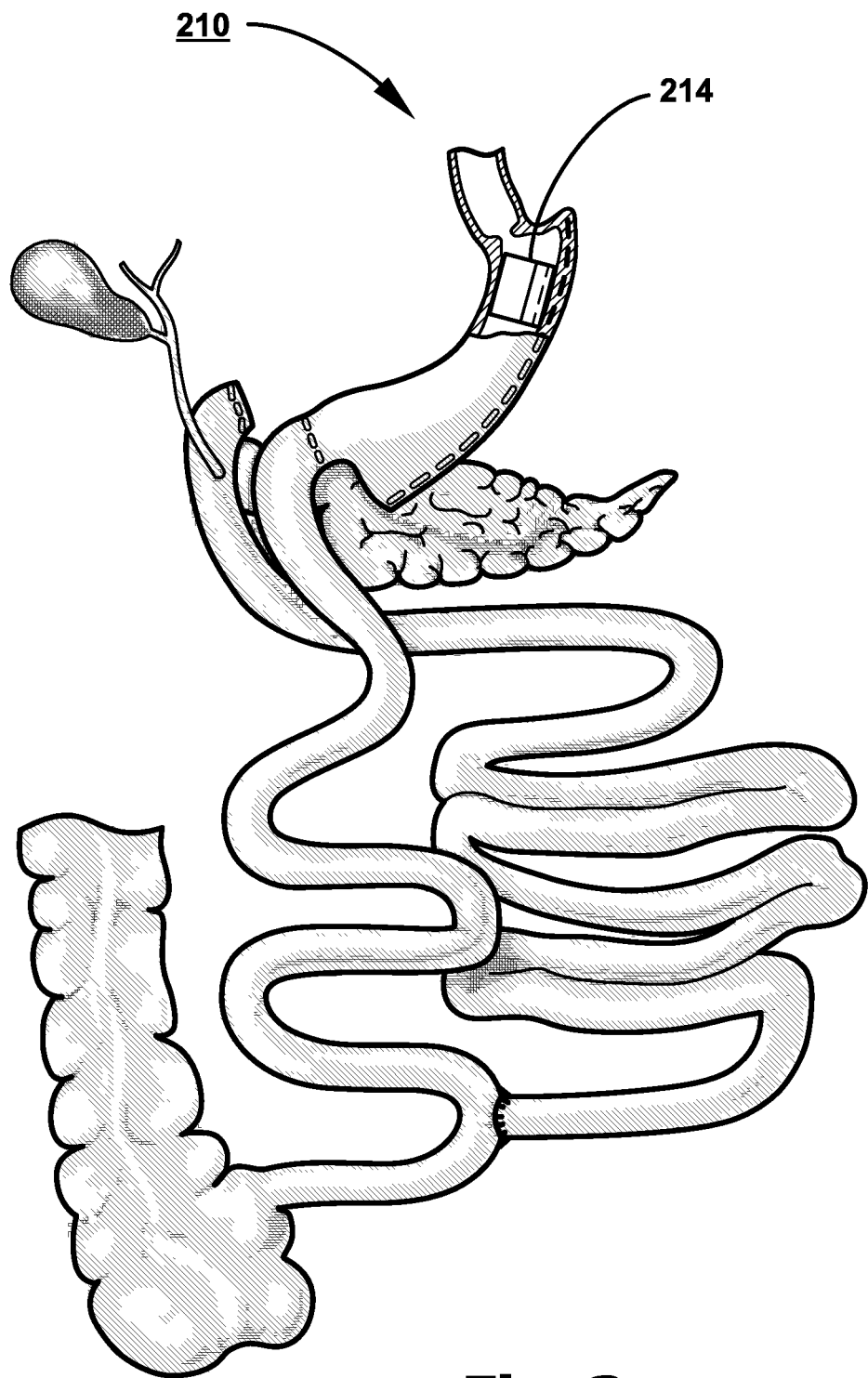
FIG. 3 is a perspective view illustrating deployment of a bariatric device in a recipient who underwent or is undergoing a duodenal switch.
Figure 4:
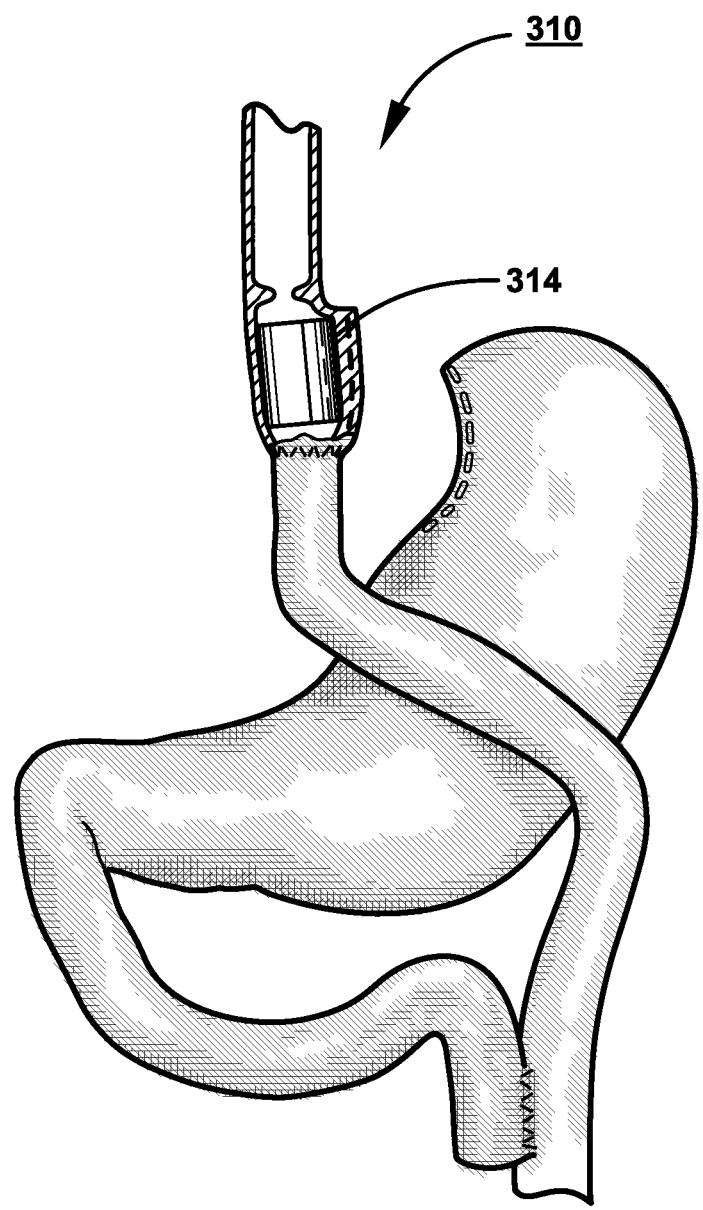
FIG. 4 is a perspective view illustrating deployment of a bariatric device in a recipient who underwent or is undergoing a gastric bypass procedure.

A bariatric device 110 is shown having a cardiac member 114 that is similar to cardiac member 14, except having a wall configured to the size and shape of the functional portion of the stomach including cardiac region of a stomach that has undergone a sleeve gastrectomy (FIG. 2). A bariatric device 210 is shown having a cardiac member 214 that is similar to cardiac members 14, 114, except having a wall configured to the size and shape of the functional portion of the stomach including the cardiac region of a stomach that has undergone a duodenal switch (FIG. 3). A bariatric device 310 is shown having a cardiac member 314 that is similar to cardiac members 14, 114, 214, except having a wall configured to generally conform to the size and shape of the functional portion of the stomach including the cardiac region of the proximal pouch of a recipient that has undergone a gastric bypass procedure, also known as a roux-en-y procedure (FIG. 4).

Although not shown, the principles disclosed herein could be used with a recipient who received a laparoscopic gastric band. In order to avoid tissue erosion at the location of the band, the cardiac member of such device may be made having an especially soft outer surface.

Provisions may be made to resist migration of cardiac member 14, 114, 214 and 314. In the case of a vertical banded gastroplasty or a roux-en-y bariatric procedure, the cardiac member may be provided having an expanded configuration that is larger than the stoma emptying the stomach pouch. In this fashion, the cardiac member will have a tendency to be retained in the pouch. For a bariatric device applied, for example, to a sleeve gastrectomy or a duodenal switch, an anti-migration mechanism may be used to resist distal migration of the cardiac member in the pouch. Such anti-migration mechanism may be in the form of suturing of the cardiac member to the wall of the stomach pouch. Such suturing may be passed through the wall of the bariatric device, through the wall of the stomach, back in through the wall of the stomach and back in through the wall of the bariatric device. By selection of the surface characteristics of the suture material and/or the wall of the cardiac member, it may be possible to assist anti-migration by promotion of tissue adhesion and/or tissue ingrowth to the device and/or suture. Alternatively, it may be possible to provide capture of the mucosa and/or muscularis of the wall of the stomach pouch utilizing the principles set forth in International Patent Application Publication No. WO 2008/100984 A2, the disclosure of which is hereby incorporated herein by reference.

Figure 5:
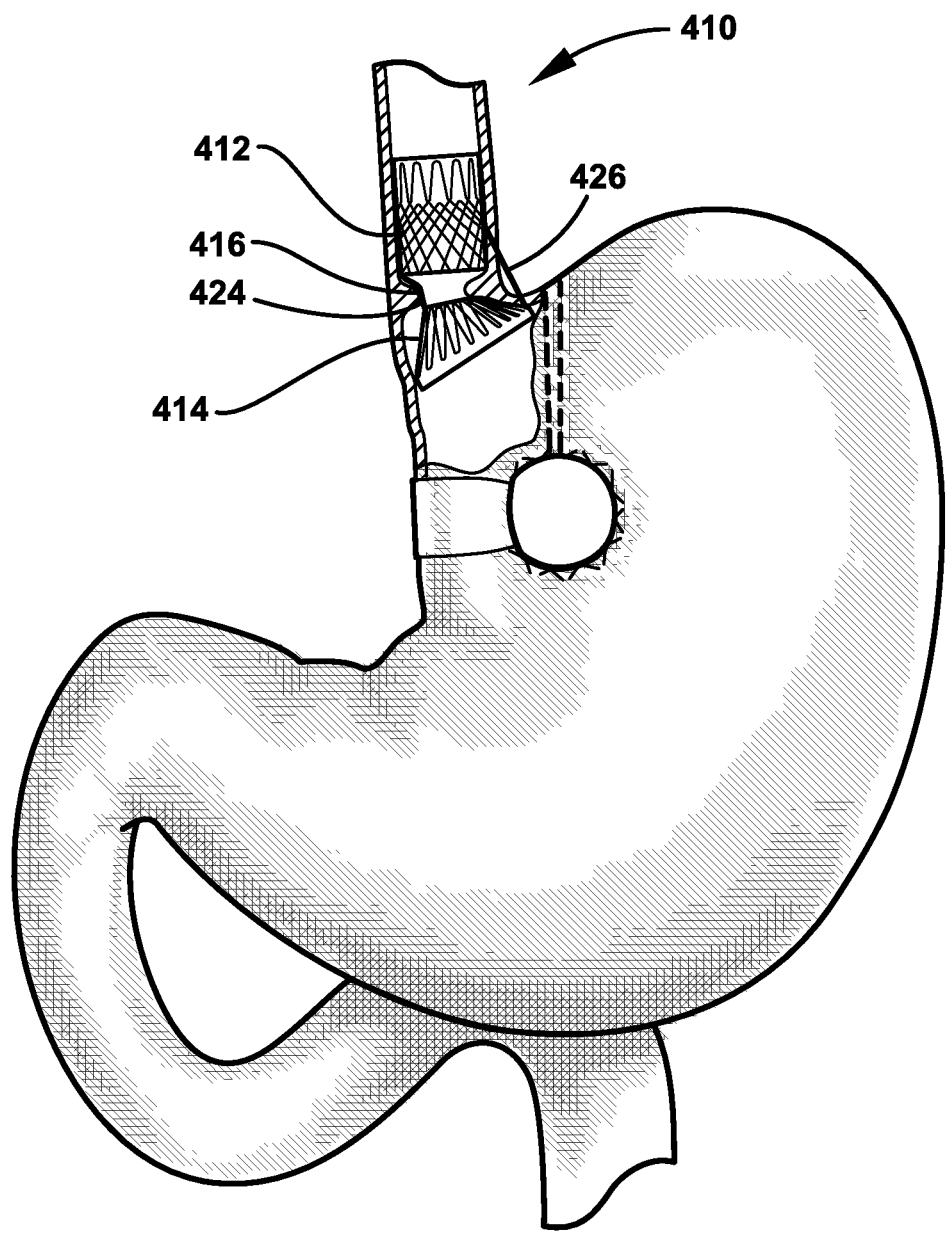
FIG. 5 is a perspective view illustrating deployment of an alternative embodiment of a bariatric device in a recipient who underwent or is undergoing a vertical banded gastroplasty.

A bariatric device 410 is shown having an esophageal member 412 having a wall configured to the size and shape of a portion of the esophagus connected by a connector 416 with a cardiac member 414 having a wall configured to the size and shape of the functional portion of the stomach including the cardiac region of a stomach that has undergone vertical banded gastroplasty (FIG. 5). Esophageal member 412 may be configured to reduce stenosis of the esophagus as disclosed in commonly assigned U.S. patent application Ser. No. 61/388,857 filed Oct. 1, 2010, by James A. Foote entitled INTRALUMINAL DEVICE AND METHOD, the disclosure of which is hereby incorporated herein by reference. Connector 416 may include a tension member 424 that passes through the gastroesophageal junction and a tether 426 that is applied in situ as disclosed in commonly assigned U.S. Patent Application Publication No. 2010/0030017 A1 entitled BARIATRIC DEVICE AND METHOD, the disclosure of which is hereby incorporated herein by reference. Alternatively, connector 416 may be of the type disclosed in International Patent Application No. PCT/US2012/038480, entitled INTRALUMINAL DEVICE AND METHOD WITH ENHANCED ANTI-MIGRATION, the disclosure of which is hereby incorporated herein by reference.

Figure 6:
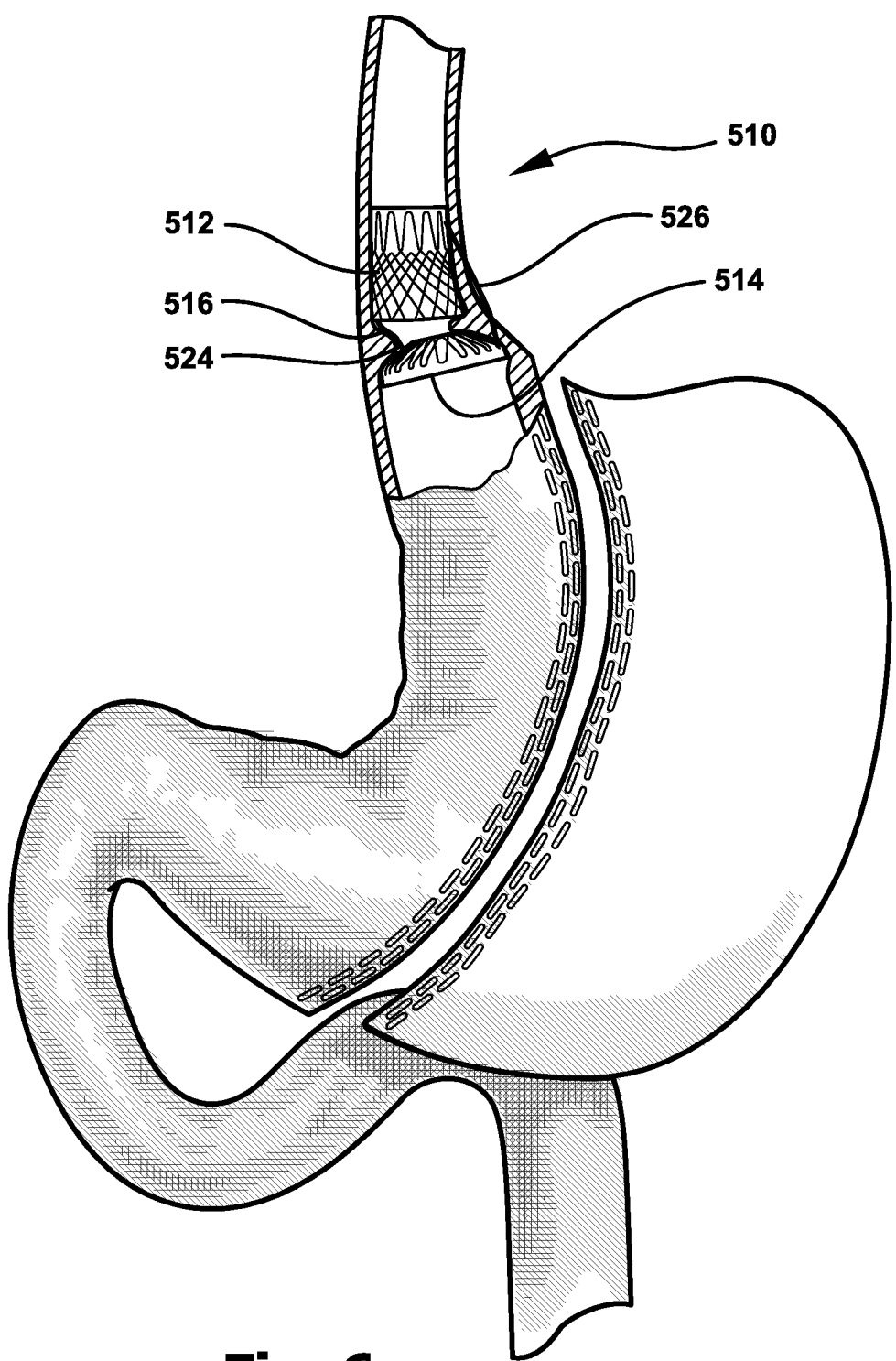
FIG. 6 is a perspective view illustrating deployment of another alternative embodiment of a bariatric device in a recipient who underwent or is undergoing a sleeve gastrectomy.

A bariatric device 510 is shown having an esophageal member 512 that is similar to esophageal member 412 having a wall configured to the size and shape of a portion of the esophagus connected by a connector 516 with a cardiac member 514 that is similar to cardiac member 414 and having a wall configured to the size and shape of the functional portion of the stomach including the cardiac region of a stomach that has undergone a sleeve gastrectomy (FIG. 6). Connector 516 has a tension member 524 and tether 526.

Figure 7:
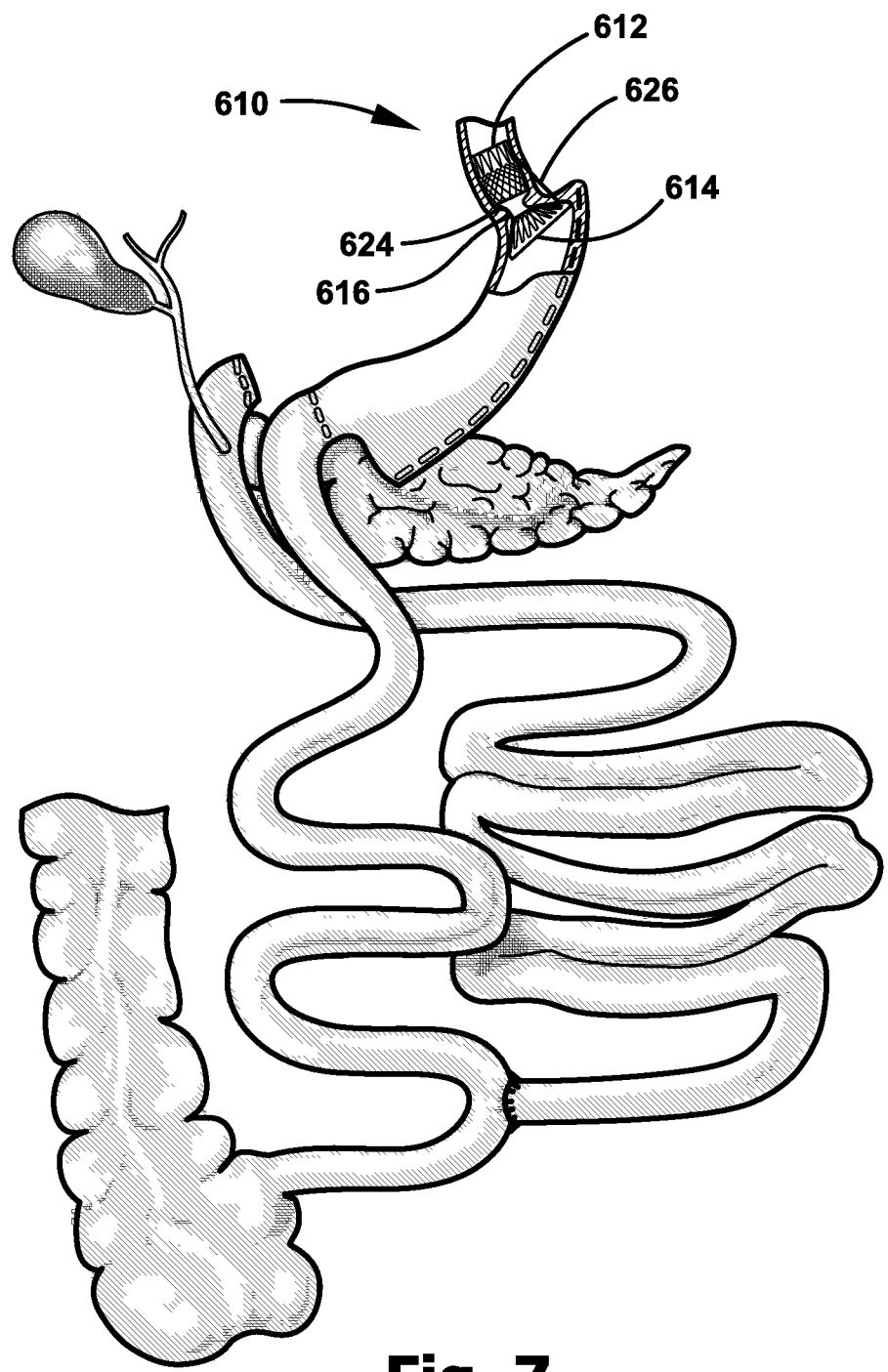
FIG. 7 is a perspective view illustrating deployment of another alternative embodiment of a bariatric device in a recipient who underwent or is undergoing a duodenal switch.

A bariatric device 610 is shown having an esophageal member 612 that is similar to esophageal member 412 having a wall configured to the size and shape of a portion of the esophagus connected by a connector 616 with a cardiac member 614 that is similar to cardiac member 414 and having a wall configured to the size and shape of the functional portion of the stomach including the cardiac region of a stomach that has undergone a duodenal switch (FIG. 7). Connector 616 has a tension member 624 and may optionally include a tether 626.

Figure 8:
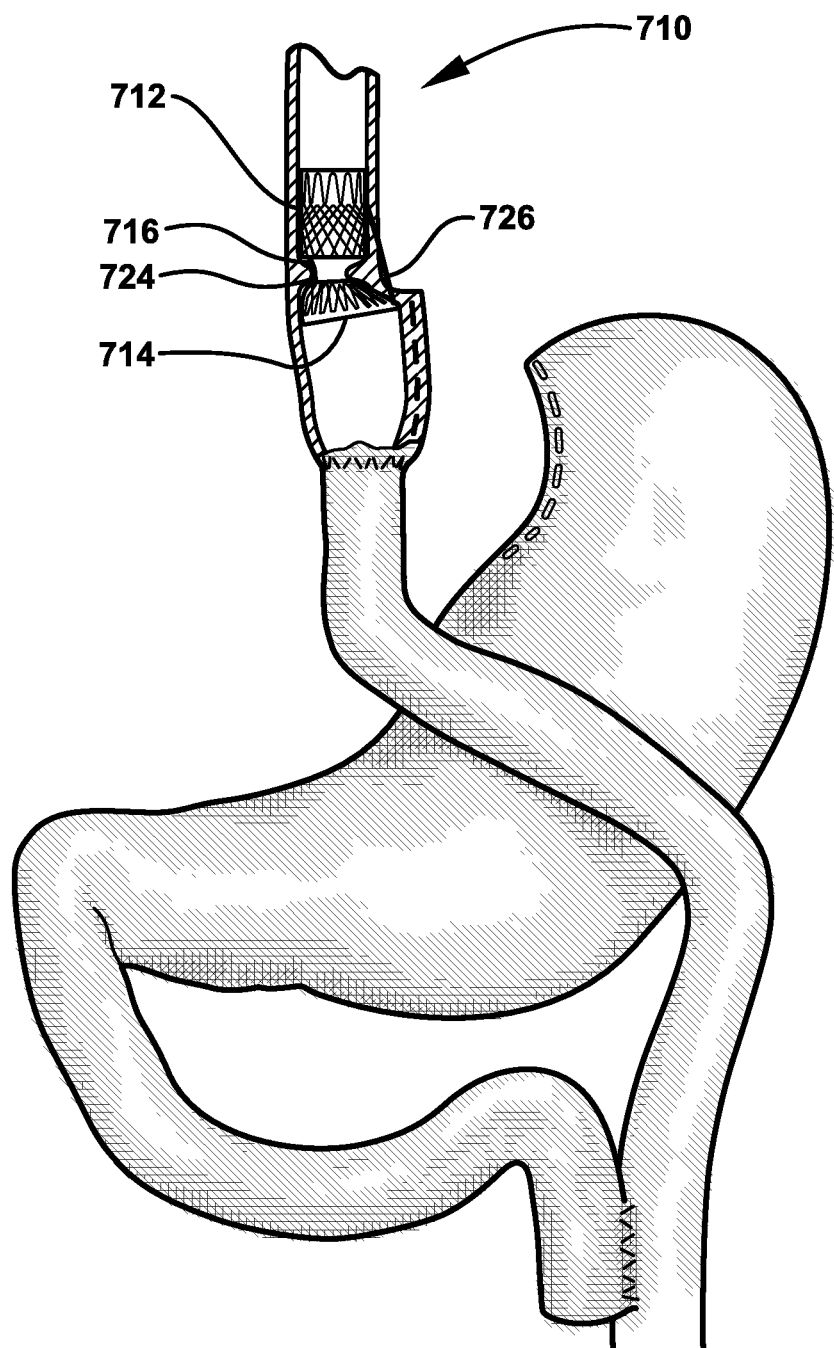
FIG. 8 is a perspective view illustrating deployment of another alternative embodiment of a bariatric device in a recipient who underwent or is undergoing a gastric bypass procedure.

A bariatric device 710 is shown having an esophageal member 712 that is similar to esophageal member 412 having a wall configured to the size and shape of a portion of the esophagus connected by a connector 716 with a cardiac member 714 that is similar to cardiac member 414 and having a wall configured to generally conform to the size and shape of the functional portion of the stomach including the cardiac region of the proximal pouch of a recipient that has undergone a gastric bypass procedure, also known as a roux-en-y procedure (FIG. 8). Connector 716 has a tension member 724 and tether 726. Other examples will become apparent to the skilled practitioner.

Esophageal members 412, 512, 612 and 712 may be provided according to the principles set forth in International Patent Application Publication No WO 2008/101048 A2, and International Patent Application No. PCT/US2012/038480, the disclosures of which is hereby incorporated herein by reference.

The strain exerted by the bariatric devices 410-710 stimulates receptors in the recipient to influence the neurohormonal feedback mechanism present at the esophagus and/or stomach pouch to cause weight loss. The strain that influences the neurohormonal feedback mechanism present at the abdominal portion of the esophagus and/or the cardiac portion of the stomach is intended to be relatively consistent over as large an area as reasonably possible.

In contrast to prior proposed devices, such as restriction devices, which require that the recipient ingest food in order to influence neurohormonal feedback mechanisms, the embodiments of the bariatric device disclosed herein are effective in the absence of food. It also augments fullness caused by food.

Figure 9:
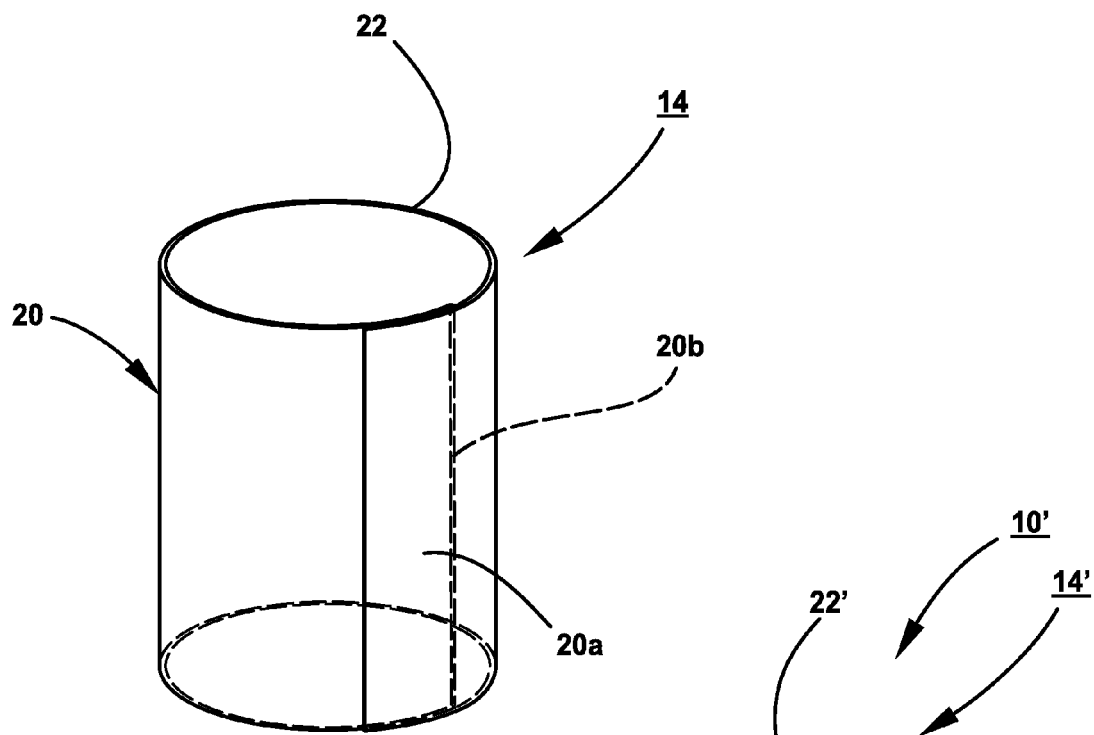
FIG. 9 is a perspective view of the bariatric device in FIG. 1.

Cardiac member 14 (or any of the embodiments of a cardiac member disclosed herein) may be defined by a wall 20 having overlapping end portions 20a, 20b (FIG. 9). Wall 20 defines an outer surface 21 that applies a strain on the stomach wall. Wall 20 further defines an opening 22 that is configured to fit against the gastroesophageal junction to restrict the passage of food between the stomach wall and surface 21. Wall 20, which may be generally cylindrical in form, is self-expanding such that end portions 20a, 20b form a scroll shape that tends to unroll outwardly to expand to the shape of the stomach pouch. End portions 20a, 20b may be compressed into a further overlapping roll form in order to be deployed orally. The degree of overlap of end portions 20a, 20b configures the size of the cardiac member to the size of the stomach pouch. Wall 20 may be formed of Nitinol wire or a die cut Nitinol sheet covered with silicone, or the like.

Wall 20 may be provided with the ability to adjust the amount of strain or force applied to the cardiac region of the stomach. This may be accomplished, for example, by providing a bladder on outer surface 21, or by otherwise incorporating a bladder into wall 20. The bladder could be filled with saline either during deployment of cardiac member 14 or subsequent to deployment, such as by using an endoscopic needle. Also, an electronic/hydraulic control may be connected to the bladder and adjusted from a control external the patient via a radio frequency link. Adjustment of the bladder in either fashion may be as disclosed in the WO 2008/101048 publication.

Adjustability of wall 20 may, alternatively, be provided, such as by a ratcheting mechanism that either brings wall end portions 20a, 20b together or spreads them apart. Such ratcheting mechanism may be mounted to wall 20 at or before deployment and accessed endoscopically at or after deployment. Alternatively, a pattern of openings may be formed in end portions 20a, 20b that can be engaged by a ratcheting mechanism having features, such as feet, that engage the openings. Such ratcheting mechanism can be deployed and adjusted endoscopically, such as after deployment.

In the case of bariatric devices 410-710, adjustability may be provided by adjusting connector 416-716 including any tension member such as a tether forming a part of the connector.

One advantage of providing adjustability to the amount of strain or force applied by wall 20 is to facilitate removal of the device from the recipient. For example, as the recipient experiences reduced excess body fat, the amount of strain or force could be reduced to acclimatize the recipient to reduced satiety provided by the device. Of course, adjustability allows the amount of satiety to be set or adjusted at the time of deployment or after deployment if the patient is experiencing too much or not enough satiety.

Figure 10:
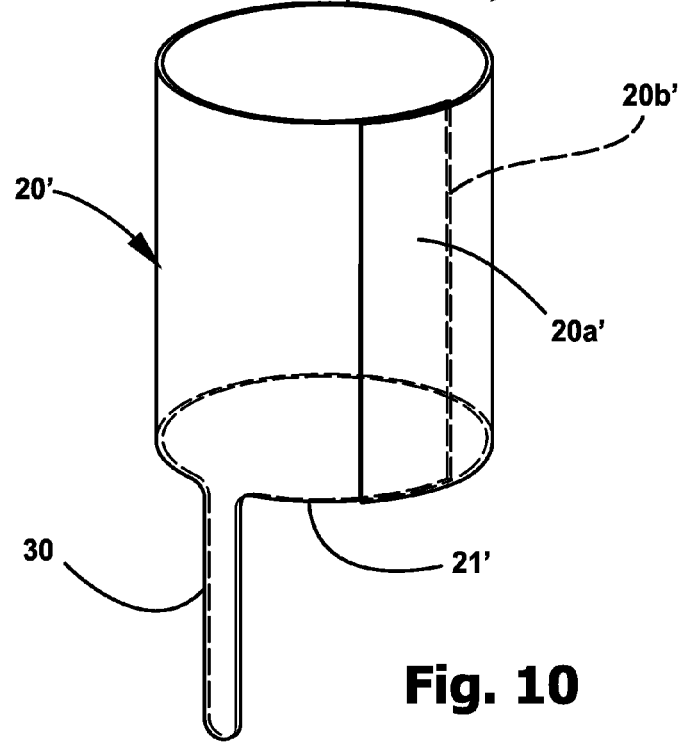
FIG. 10 is the same view as FIG. 9 of an alternative embodiment thereof.

In an alternative embodiment shown in FIG. 10, bariatric device 10' includes a cardiac member 14' that is similar to cardiac member 14 except that wall 20 includes a projection 30 that is configured to extend either distally into the intestine or proximally into the esophagus. Projection 30 may be affixed, such as by suturing, stapling, mucosal capture, or the like. Projection 30 ensures proper orientation of cardiac member 10' with the openings at end portions 20a' and 20b' aligned with the respective openings at the GE junction and pylorus.

The bariatric devices disclosed herein may be made in whole or in part from bioabsorbable materials or from non-absorbable materials. The tissue attachment, tissue ingrowth and/or mucosal capture, which results from the tissue essentially at least partially incorporating certain embodiments of the bariatric device into the anatomy of the recipient, may provide resistance to the formation of microbial biofilm and thereby reduces the potential for infection, odor, and the like. As with all anti-migration fixation techniques described herein, these may be used in combination with other fixation techniques. These anchoring techniques may be used to promote long-term deployment by incorporating the device into the body of the recipient.

Thus, it is seen that the disclosed embodiment provides a new category of weight loss techniques. The embodiment advantageously utilizes mechanoreceptors, such as tension receptors, stretch receptors and/or baroreceptors, such as those located at the cardiac portion of the stomach of the recipient to cause weight loss. The disclosed embodiments facilitate burping and vomiting and do not substantially interfere with other functions of the GE junction pseudo-sphincter. Use with a recipient having undergone bariatric surgery in the past or concurrently with receiving the embodiments of the bariatric device disclosed herein augment the effect of the bariatric procedure which may utilize the presence of solid food to create satiety.

Changes and modifications in the specifically described embodiments can be carried out without departing from the principles of the invention which is intended to be limited only by the scope of the appended claims, as interpreted according to the principles of patent law including the doctrine of equivalents.

The invention claimed is:

1. A bariatric device, comprising:
   a cardiac member having a cardiac surface that is configured to generally conform to the shape and size of a functional portion of the stomach that includes the cardiac region of the stomach of a recipient with an altered stomach; and
   said cardiac member being adapted to apply tension to the cardiac region of the stomach to stimulate receptors in order to influence a neurohormonal mechanism in the recipient sufficient to cause at least partial satiety by augmenting fullness caused by food and simulating fullness in the absence of food.

2. The bariatric device as claimed in claim 1 wherein said cardiac member is configured to the size and shape of the functional portion of the stomach that includes the cardiac region of the stomach of a recipient having undergone at least one chosen from (i) a gastric bypass procedure, (ii) a vertical banded gastroplasty, (iii) a sleeve gastrectomy, and (iv) a duodenal switch.

3. The bariatric device as claimed in claim 1 wherein said cardiac member has a self-expanding surface.

4. The bariatric device as claimed in claim 3 wherein said self-expanding surface is scroll-shaped to allow said self-expanding surface to be contracted in a roll.

5. The bariatric device as claimed in claim 1 including an esophageal member having an esophageal surface that is configured to generally conform to the shape and size of a portion of the esophagus and a connector connected with said esophageal member and said cardiac member.

6. The bariatric device as claimed in claim 5 wherein said cardiac member is configured to the size and shape of the functional portion of the stomach that includes the cardiac region of the stomach of a recipient having undergone at least one chosen from (i) a gastric bypass procedure, (ii) a vertical banded gastroplasty, (iii) a sleeve gastrectomy, and (iv) a duodenal switch.

7. The bariatric device as claimed in claim 5 wherein said bariatric device is adjustable.

8. The bariatric device as claimed in claim 1 including an anti-migration mechanism that comprises at least one chosen from (i) a tissue adhesion surface, (ii) a tissue ingrowth surface, (iii) said cardiac member being generally larger in shape than a stoma of the native stomach, and (iv) a structure that is configured to capture at least the mucosa of the stomach wall or the esophageal wall.

9. The bariatric device as claimed in claim 1 including a projection from said cardiac member, said projection configured to extend to the esophagus or the intestine of the recipient to resist misorientation of said bariatric device.

10. The bariatric device as claimed in claim 1 wherein said bariatric device is adjustable.

11. The bariatric device as claimed in claim 1 wherein said cardiac member is adapted to apply outward pressure to the cardiac region of the stomach.

12. A method of causing at least partial satiety in a recipient, comprising:
   deploying a bariatric device to the functional portion of the stomach of a recipient having an altered stomach, said bariatric device comprising a cardiac member having a cardiac surface that is configured to generally conform to the shape and size of the functional portion of the altered stomach that includes the cardiac region of the stomach of the recipient; and
   stimulating receptors with said cardiac surface including applying tension to the cardiac region of the stomach in order to influence a neurohormonal mechanism in the recipient sufficient to cause at least partial satiety by augmenting fullness caused by food and simulating fullness in the absence of food.

13. The method as claimed in claim 12 wherein said applying tension comprises applying outward pressure to the cardiac region of the stomach.

14. The method as claimed in claim 12 including deploying said bariatric device to the functional portion of the stomach that includes the cardiac region of the stomach of a recipient having undergone at least one chosen from (i) a gastric bypass procedure, (ii) a vertical banded gastroplasty, (iii) a sleeve gastrectomy, and (iv) a duodenal switch.

15. The method as claimed in claim 12 wherein said cardiac member has a self-expanding surface.

16. The method as claimed in claim 15 wherein said self-expanding surface is scroll-shaped to allow said self-expanding surface to be contracted in a roll.

17. The method as claimed in claim 12 wherein said bariatric device has an esophageal member comprising an esophageal surface that is configured to generally conform to the shape and size of a portion of the esophagus and a connector connected with said esophageal member and said cardiac member.

18. The method as claimed in claim 17 including deploying said bariatric device to the functional portion of the stomach that includes the cardiac region of the stomach of a recipient having undergone at least one chosen from (i) a gastric bypass procedure, (ii) a vertical banded gastroplasty, (iii) a sleeve gastrectomy, and (iv) a duodenal switch.

19. The method as claimed in claim 17 including adjusting the amount of stimulating with said bariatric device.

20. The method as claimed in claim 12 wherein said bariatric device includes an anti-migration mechanism that includes at least one chosen from (i) a tissue adhesion surface, (ii) a tissue ingrowth surface, (iii) said cardiac member being generally larger in shape than a stoma of the native stomach and (iv) is configured to capture at least mucosa of the stomach wall or esophageal wall.

21. The method as claimed in claim 12 wherein said cardiac member includes a projection that is configured to extend to the esophagus or the intestine of the recipient to resist misorientation of said bariatric device.

22. The method as claimed in claim 12 including adjusting the amount of stimulating with said bariatric device.

* * * * *